(12) United States Patent
Shi et al.

(10) Patent No.: US 7,081,261 B2
(45) Date of Patent: *Jul. 25, 2006

(54) RESISTANT STARCH PREPARED BY ISOAMYLASE DEBRANCHING OF LOW AMYLOSE STARCH

(75) Inventors: Yong-Cheng Shi, Hillsborough, NJ (US); Xiaoyuan Cui, Belle Mead, NJ (US); Anne M. Birkett, Somerville, NJ (US); Michael G. Thatcher, Bridgewater, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 201 days.

This patent is subject to a terminal disclaimer.

(21) Appl. No.: 10/145,186

(22) Filed: May 14, 2002

(65) Prior Publication Data

US 2003/0215561 A1 Nov. 20, 2003

(51) Int. Cl.
*A23L 1/105* (2006.01)
*A23L 1/0522* (2006.01)
*C08B 30/12* (2006.01)

(52) U.S. Cl. .......................... 426/28; 426/52; 426/661; 127/32

(58) Field of Classification Search .................. 127/32, 127/71; 426/19, 28, 64, 52, 661
See application file for complete search history.

(56) References Cited

U.S. PATENT DOCUMENTS

| | | | |
|---|---|---|---|
| 3,490,742 A | 1/1970 | Nichols et al. | |
| 3,622,677 A | 11/1971 | Short et al. | |
| 3,881,991 A | 5/1975 | Kurimoto et al. | |
| 4,072,535 A | 2/1978 | Short et al. | |
| 4,384,005 A | 5/1983 | McSweeney | |
| 4,551,177 A | 11/1985 | Trubiano et al. | |
| 4,971,723 A | 11/1990 | Chiu | |
| 5,051,271 A | 9/1991 | Iyengar et al. | |
| 5,194,284 A | 3/1993 | Chiu et al. | |
| 5,281,276 A | 1/1994 | Chiu et al. | |
| 5,395,640 A | 3/1995 | Harris et al. | |
| 5,409,542 A * | 4/1995 | Henley et al. | |
| 5,409,726 A * | 4/1995 | Stanley et al. | 426/573 |
| 5,468,286 A * | 11/1995 | Wai-Chiu et al. | |
| 5,585,114 A * | 12/1996 | Besemer et al. | |
| 5,629,018 A * | 5/1997 | Besemer et al. | |
| 5,776,887 A * | 7/1998 | Wibert et al. | |
| 5,962,047 A * | 10/1999 | Gross et al. | |
| 6,010,717 A * | 1/2000 | Arends-Scholte et al. | |
| 6,086,917 A * | 7/2000 | Trubiano et al. | |
| 6,090,594 A | 7/2000 | Kettlitz et al. | |
| 6,248,375 B1 * | 6/2001 | Gilles et al. | |
| 2002/0012733 A1 * | 1/2002 | Kester et al. | |
| 2003/0054501 A1 | 3/2003 | Schmiedel et al. | |

FOREIGN PATENT DOCUMENTS

| | | |
|---|---|---|
| EP | 0 499 648 | 12/1993 |
| EP | 0 512 249 B1 | 3/1999 |
| EP | 0 692 252 B1 | 4/2001 |
| EP | 0 846 704 B1 | 3/2002 |
| WO | WO 97/31627 | 9/1997 |
| WO | WO 99/02042 | 1/1999 |
| WO | WO 99/09066 | 2/1999 |
| WO | WO 00/55209 | 9/2000 |
| WO | WO 01/17370 | * 3/2001 |
| WO | WO 01/64255 | * 9/2001 |

OTHER PUBLICATIONS

Szczodrak, J. and Y. Pomeranz, "Starch and Enzyme-Resistant Starch from High-Amylose Barley", Cereal Chem., 68 (6): 589-596, 1991.

Englyst et al., "Classification and measurement of nutritionally important starch fractions", European Journal of Clinical Nutrition (1992) 46 (Suppl. 2), S33-S50.

Guraya et al., "Effect of Cooling, and Freezing on the Digestibility of Rice Starch and Physical Properties of the Resulting Material", Starch/Stärke 53 (2001), pp. 64-74.

Guraya et al., "Effect of Enzyme Concentration and Storage Temperature on the Formation of Slowly Digestible Starch from Cooked Debranched Rice Starch", Starch/Starke 53 (2001), pp. 131-139.*

FAO Food and Nutrition Paper 66, "Carbohydrates in human nutrition", Chapter 4—The Role of the Glycemic Index in Food Choice, pp. 25-30, Report from Apr. 14-18, 1997.*

* cited by examiner

*Primary Examiner*—Keith Hendricks
(74) *Attorney, Agent, or Firm*—Karen G. Kaiser

(57) ABSTRACT

This patent pertains to a resistant starch prepared by fully debranching a low amylose starch using isoamylase. Such resistant starch is useful in edible products, including nutritional supplements.

18 Claims, No Drawings

RESISTANT STARCH PREPARED BY ISOAMYLASE DEBRANCHING OF LOW AMYLOSE STARCH

BACKGROUND OF THE INVENTION

The present invention relates to a resistant starch prepared by isoamylase debranching of low amylose starches to form a completely linear short chain α-glucan composition, and its use.

Starch, a complex carbohydrate, is composed of two types of polysaccharide molecules, amylose, a mostly linear and flexible polymer of D-anhydroglucose units that are linked by alpha-1,4-D-glucosidic bonds, and amylopectin, a branched polymer of linear chains that are linked by alpha-1,6-D-glucosidic bonds. Starch is digested predominantly in the small intestine by the enzyme alpha-amylase.

It is known that certain starch processing operations result in the transformation of starch into starch that is resistant to enzymatic hydrolysis within the small intestine, known simply as resistant starch. Resistant starch resists digestion and absorption in the small intestine, and passes into the large intestine where it is fermented by colonic microflora to short chain fatty acids, particularly butyrate, and gases.

Research literature indicates that this fermentation of resistant starch by colonic bacteria has numerous beneficial effects and thus would be useful for both food and drug applications.

Resistant starch may be used in foods, including medical foods and dietary supplements, to maintain colonic health and mucosal integrity. Resistant starch is known as a prebiotic. Further, as it is not utilized until it reaches the large intestine where it is fermented to short chain fatty acids, resistant starch has a reduced caloric value. The reduction in available or glycemic carbohydrate in the small intestine has been linked to improved blood glucose and insulin control, with associated benefits for weight management. Research also indicates that resistant starches may contribute to maintaining a healthy immune system in humans.

Resistant starch may also be used as a drug. It has been linked to a decreased risk for various colonic diseases, including a decreased incidence of cancer. In addition, resistant starch may reduce the risk of the cluster of metabolic disorders associated with Syndrome X including insulin resistance, hyperglycemia, hyperinsulinemia, dyslipidemia, dysfibrinolysis, diabetes, hypertension and cardiovascular disease. It may also be useful for treating obesity.

Resistant starch (RS) has been classified in the literature into four categories depending on the causes of resistance. RS1 is a physically inaccessible starch due to entrapment of granules within a protein matrix or within a plant cell wall. RS2 is a granular starch that resists digestion by pancreatic alpha-amylase. RS3 is a retrograded, nongranular starch or starch food. RS4 is a resistant starch that has linkages other than alpha-1,4- and alpha-1,6-D-glucosidic bonds.

Various methods have been reported for producing the various types of resistant starch. These include U.S. Pat. No. 5,593,503 which describes a method of making a granular resistant starch; and U.S. Pat. Nos. 5,281,276 and 5,409,542 which describe methods of making resistant starches of the RS3-type, all from high amylose starches. U.S. Pat. No. 5,855,946 describes a method of making a resistant starch of the RS4-type by crosslinking and phosphorylating starch. U.S. Pat. No. 6,043,229 discloses a partially degraded and retrograded resistant starch.

Surprisingly, it has now been discovered that completely linear, short chain alpha-1,4-glucans which are highly crystallized result in a starch which is resistant to amylase digestion.

SUMMARY OF THE INVENTION

This patent pertains to a resistant starch prepared by fully debranching a low amylopectin starch using isoamylase. Such resistant starch is useful in edible products, including nutritional supplements.

Dextrose equivalent, as used herein, is intended to mean the reducing power of the hydrolysate. Each starch molecule has one reducing end; therefore DE is inversely related to molecular weight. The DE of anhydrous D-glucose is defined as 100 and the DE of unhydrolyzed starch is virtually zero.

Fully or completely debranched starch, as used herein, is intended to mean that which theoretically comprises 100%, by weight, of short chain amylose and, in practice, that which is so highly debranched that further enzyme activity produces no measurable change in the percentage of short chain amylose.

As used herein, a prebiotic is intended to mean a resistant starch that beneficially affects the host by selectively stimulating the growth and/or activity of one or a limited number of bacteria in the colon, and thus improves host health.

As used herein, the term resistant starch is intended to mean the sum of starch and products of starch degradation not absorbed in the small intestine of healthy individuals.

As used herein, the term short chain amylose refers to linear polymers containing from about 5 to 65 anhydroglucose units linked by alpha-1,4-D-glucoside bonds.

DETAILED DESCRIPTION OF THE INVENTION

This patent pertains to a resistant starch prepared by fully debranching a low amylopectin starch using isoamylase. Such resistant starch is useful in edible products, including nutritional supplements.

Starch, as used herein, is intended to include all starches derived from any native source, any of which may be suitable for use herein. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be the waxy variety of corn (maize), pea, potato, sweet potato, banana, barley, wheat, rice, oat, sago, amaranth, tapioca, arrowroot, canna, and sorghum, particularly maize, potato, cassava, and rice, more particularly maize or potato, cassava, and rice. As used herein, the term "waxy" or "low amylose" is intended to include a starch containing no more than about 10% by weight amylose. Particularly suitable in the invention are those starches which contain no more than about 5% amylose by weight.

The starch is completely hydrolyzed by isoamylase. The enzymatic hydrolysis of the starch base is carried out using techniques known in the art. The amount of enzyme used is dependent upon the enzyme source and activity and base material used. Typically, the enzyme is used in an amount of from about 0.05 to about 2%, particularly from about 0.1 to about 0.4%, by weight of the starch.

The optimum parameters for enzyme activity will vary depending upon the enzyme used. The rate of enzyme degradation depends upon factors known in the art, including the enzyme concentration, substrate concentration, pH, temperature, the presence or absence of inhibitors, and the degree and type of modification if any. These parameters may be adjusted to optimize the digestion rate of the starch base.

The starch is gelatinized using techniques known in the art before isoamylase hydrolysis. Techniques known in the art include without limitation those disclosed for example in U.S. Pat. Nos. 4,465,702, 5,037,929, 5,131,953, and 5,149,799. Also see, Chapter XXII—"Production and Use of Pregelatinized Starch", *Starch: Chemistry and Technology*, Vol. III—Industrial Aspects, R. L. Whistler and E. F. Paschall, Editors, Academic Press, N.Y. 1967. The gelatinization process unfolds the starch molecules from the granular structure, thereby permitting the enzyme to more easily and uniformly degrade the starch molecules.

Generally the enzyme treatment is carried out in an aqueous or buffered slurry at a starch solids level of about 10 to about 40%, depending upon the base starch being treated. A solids level of from about 15 to 35% is particularly useful, from about 18 to 30% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 25 to about 70° C. is used, particularly from about 50 to about 60° C. In general, the pH is adjusted to about 3.0 to about 6.0, particularly from about 3.5 to about 4.5, using techniques known in the art.

The enzyme reaction is continued until the starch is completely debranched. In general, the enzyme reaction will take from about 1 to about 24 hours, particularly about 4 to about 12 hours. The time of the reaction is dependent upon the type of starch used, the amount of enzyme used, and the reaction parameters of solids percent, pH, and temperature.

The amount of hydrolysis may be monitored and defined by measuring the concentration of reducing groups which are freed by alpha-1,6-D-glucanohydrolase activity by methods well known in the art. Other techniques such as monitoring the change in viscosity, iodine reaction, or the change in molecular weight may be used to define the reaction end point. When the starch is completely debranched, the monitored measurement will no longer change. Typically, the starch will be completely debranched when it has been at least about 95%, more particularly at least about 98%, most particularly at least about 99% debranched by weight. The debranched starch will typically have an average chain length of 14–25 glucose units and less than about 0.2%, particularly less than about 0.1% alpha-1,6-D-glucosidic bonds (linkages).

Optionally, the enzyme may be deactivated (denatured) by any technique known in the art such as heat, acid or base deactivation. For example, acid deactivation may be accomplished by adjusting the pH to lower than 3.0 for at least 30 minutes or heat deactivation may be accomplished by raising the temperature to from about 80 to about 90° C. and maintaining it at that temperature for at least about 20 minutes to fully deactivate the enzyme.

The starches may be converted either prior to or after isoamylase debranching, and is intended to include fluidity or thin-boiling starches prepared by oxidation, acid hydrolysis, heat and or acid dextrinization. These processes are well known in the art.

The starch may be further modified, either before or after the enzymatic hydrolysis. Such modification may be physical, enzymatic, or chemical. Physical modification includes by shearing or thermal inhibition, for example by the process described in U.S. Pat. No. 5,725,676.

The starch may be chemically modified, including without limitation, crosslinked, acetylated and organically esterified, hydroxyethylated and hydroxypropylated, phosphorylated and inorganically esterified, cationic, anionic, nonionic, and zwitterionic, and succinate and substituted succinate derivatives thereof. Such modifications are known in the art, for example in *Modified Starches: Properties and Uses*, Ed. Wurzburg, CRC Press, Inc., Fla. (1986).

Any starch base having suitable properties for use herein may be purified by any method known in the art to remove starch off flavors and colors that are native to the polysaccharide or created during processing. Suitable purification processes for treating starches are disclosed in the family of patents represented by EP 554 818 (Kasica, et al.). Alkali washing techniques are also useful and described in the family of patents represented by U.S. Pat. No. 4,477,480 (Seidel) and U.S. Pat. No. 5,187,272 (Bertalan et al.). The debranched starch may also be purified by such methods.

The resultant solution is typically adjusted to the desired pH according to its intended end use. In general, the pH is adjusted to from about 5.0 to about 7.5, particularly from about 6.0 to about 7.0, using techniques known in the art. Further, any short chain amylose which precipitated out of the starch dispersion may be redispersed. If purification of the debranched starch composition is desired, reaction impurities and by-products may be removed by dialysis, filtration, centrifugation or any other method known in the art for isolating and concentrating starch compositions. For example, the degraded starch may be washed using techniques known in the art to remove soluble low molecular weight fractions, such as oligosaccharides, resulting in more highly crystalline starch.

The debranched starch is allowed to crystallize by methods known in the art, for example by allowing the starch to stand and retrograde. The starch is then recovered using methods known in the art, particularly by filtration or by drying, including spray drying, freeze drying, flash drying or air drying, more particularly by filtration or flash drying. It is important to control the crystallization, typically by controlling retrogradation and drying, in order to obtain the high degree of crystallinity essential to the present invention. It is further important that the method of drying and other post-crystallization processes do not substantially destroy the crystals.

The resultant debranched starch is in the form highly crystalline short chain amylose from the debranched starch and is uniquely functional as a resistant starch. The starch is characterized by a resistant starch content of at least about 70%, particularly at least about 75%, by weight using the methodology described, infra.

The starch is also characterized by a peak melting point temperature, Tp, as measured by DSC using the procedure described infra, of at least about 90° C., more particularly at least about 100° C., most particularly at least about 110° C. The starch is also characterized by an enthalpy, ΔH, as measured by DSC using the procedure described infra, of at least about 25 J/g, particularly at least about 30 J/g. Such DSC values are indicative of the highly crystalline nature of the product.

The debranched starch is further characterized by a dextrose equivalent (DE) of at least about 5.0, more particularly of at least 6.0, most particularly at least about 7.0. However, a lower dextrose equivalent (e.g. a DE of at least about 4.0) may be achieved by altering the processing conditions, particularly by removing the low molecular weight hydrolysis products.

It is process tolerant in that the level of resistance does not significantly decrease during processing, including heat.

The starch is uniquely functional as a resistant starch and may be used in a variety of edible products. Edible products is intended to include, without limitation: cereal, bars, pizza, pasta, dressings, including pourable dressings and spoonable dressings; pie fillings, including fruit and cream fillings; sauces, including white sauces and dairy-based sauces such as cheese sauces; gravies; lite syrups; puddings; custards; yogurts; sour creams; beverages, including dairy-based beverages; glazes; baked goods, including crackers, breads, muffins, bagels, biscuits, cookies, pie crusts, and cakes; condiments, confectioneries and gums, and soups.

Edible products also is intended to include nutritional and medical foods and beverages, including dietetic or weight loss products, diabetic products, products for sustained energy release such as sports drinks and power bars, meal replacements, and nutritional supplements. Such nutritional products is intended to include dietetic products, diabetic products, and prebiotics.

The present starch may be added in any amount desired or necessary to obtain the functionality of the composition. In general, the starch may be added in an amount of from about 0.01% to about 100%, particularly from about 1 to about 50%, by weight of the composition. The starch may be added to the food or beverage in the same manner as any other starch, typically by mixing directly into the product or adding it in the form of a sol.

EXAMPLES

The following examples are presented to further illustrate and explain the present invention and should not be taken as limiting in any regard. All percents used are on a weight/weight basis.

The following test procedures are used throughout the examples:

Differential scanning calorimetry—Differential scanning calorimetry measurements were performed in a Perkin-Elmer DSC-7 (Norwalk, Conn., U.S.A). The instrument was calibrated with indium. Samples of approximately 10 mg starch at a starch:water ratio of 1:3 are prepared and heated at 10° C./min from 50° C. to 160° C. An empty stainless steal pan is used as a reference.

Chain Length and Linearity—The debranched starch samples were analyzed using NMR to determine the average chain length and alpha-1,4 to alpha-1,6 linkage ratios. The NMR samples were prepared by suspending 5–6 mg of the starch in 2.5 mL of $D_2O$/TSP (sodium trimethyl silyl propionate) and pressure cooking the suspensions for approximately 1 hour. The resulting clear solutions were transferred to 5 mm NMR tubes and kept hot on a steam bath until the NMR spectra were acquired. This procedure for the handling of the samples insured that the crystalline starch material remained in solution. The proton NMR spectra were acquired at 90° C. on a Bruker DPX-400 spectrometer at 400 MHz.

The chemical shift assignments (relative to TSP at 90° C.) for the resonance of interest were as follows. The alpha-1,4 mid-chain linkages had a chemical shift of 5.38 ppm, the alpha-1,6 mid-chain (branch points) at 4.96 ppm, the alpha-form of the reducing end groups at 5.23 ppm, and the beta-form of the reducing end groups at 4.65 ppm.

The average chain length for the starch samples was calculated from the ratio of the reducing end groups to the mid-chain resonance. The percentage of alpha-1,6 linkages (branch points) were calculated from the amount of alpha-1,6 linkages versus alpha-1,4 linkages.

Dextrose Equivalent (DE)—For in-process DE measurement, the Fehling Volumetric Titration Method was used. A 500 ml Erlenmeyer flask was rinsed with deionized (D.I.) water. 50 ml of D.I. water was then added. The addition of 5 ml each of Fehling Solutions A and B, and 2 drops of methylene blue with two boiling chips followed. After determination of the reaction solids using a Refractometer, a starch solution containing 2–4 percent starch solids was prepared using D.I. water by diluting the reaction solution in a beaker. Before proceeding to the next step, the solids were checked by a Refractometer to make sure the solution was prepared correctly. The beaker with starch solution was weighed and the weight recorded. 15 grams of the starch solution was added into the Erlenmeyer flask with prepared Fehlings solution. After they were boiled under agitation for 2 minutes on a hot plate, a bluish tint normally appeared. Starch solution from the beaker was added using a pipette gradually until the bluish tint disappeared and a distinctive reddish cuprous oxide formed. The starch solution was continuously stirred with a plastic pipette to keep the solution uniform. When the reddish endpoint was reached, the beaker containing starch solution was weighed again to determine the weight of starch consumed. The calculation of D.E. can be seen from following equation:

$$D.E. = \frac{[\text{Fehling factor} \times 100]}{[(\text{grams required from starch solution}) \times (\text{conc. of starch solution})]}$$

Simulated Digestion—(Englyst et al, European Journal of Clinical Nutrition, 1992, 46,S33-S50)—Food samples are ground/minced as if masticated. Powder starch samples are screened to a particle size of 250 microns or less. A 500–600 mg±0.1 mg of sample is weighed and added to the sample tube. 10 ml of a pepsin (0.5%), guar gum (0.5%), and HCl (0.05 M) solution is added to each tube.

Blank and glucose standard tubes are prepared. The blank is 20 ml of a buffer containing 0.25 M sodium acetate and 0.02% calcium chloride. Glucose standards are prepared by mixing 10 ml sodium acetate buffer (described above) and 10ml of 50 mg/ml glucose solution. Standards are prepared in duplicate.

The enzyme mix is prepared by adding 18 g of porcine pancreatin (Sigma P-7545) to 120 ml of deionized water, mixing well, then centrifuging at 3000 g for 10 minutes. The supernatant is collected and 48 mg of dry invertase (Sigma I-4504) and 0.5 ml AMG 400 (Novo Nordisk) are added.

The sample tubes are pre-incubated at 37° C. for 30 min, then removed from the bath and 10 ml of sodium acetate buffer is added along with glass balls/marbles (to aid in physical breakdown of the sample during shaking).

5 ml of enzyme mixture is added to the samples, blank, and standards. The tubes are shaken horizontally in a 37° C. waterbath at approximately 180 strokes/min. Time "zero" represents the first addition of the enzyme mixture to the first tube.

After 20 and 120 minutes, 0.5-ml aliquots are removed from the incubating samples and placed into a separate tube of 20 ml 66% ethanol (to stop the reaction). After 1 hour, an aliquot is centrifuged at 3000 g for 10 minutes.

The glucose concentration in each tube is measured using the glucose oxidase/peroxidase method (Megazyme *Glucose Assay Procedure* GLC9/96). This is a colorimetric procedure. HPLC may also be used to detect glucose as disclosed in previous literature using this experiment.

The degree of starch digestion is determined by calculating the glucose concentration against the glucose standards, using a conversion factor of 0.9. Results are given as "% starch digested" (dry weight basis) after 20 and 120 minutes. RS (resistant starch) is 100% minus the 120 minute value.

Every sample analysis batch includes a reference sample of uncooked cornstarch. The accepted range of % digestion values for cornstarch are:

| Sample | s20 | s120 | RS |
|---|---|---|---|
| Cornstarch[1] | 17.5 ± 2.5 | 80 ± 5 | approx. 47.5 |

[1]Melogel ® starch, commercially available from National Starch and Chemical Company, Bridgewater, NJ, USA.

Cooked Models—A model is used to mimic commercial food processing at low moisture. The model uses starch in water at 50% solids and bakes the paste in an oven at 190° C. for approximately 20 minutes. The sample is then ground and screened to a particle size of 250 microns or less.

Example 1

Preparation of Resistant Corn Starch

A. 10 kg of waxy maize starch was slurried in 30 liters of water. The slurry was jet-cooked with full steam at 310–315° F. (154.4–157.2° C.) and 80 psi ($5.52 \times 10^5$ Pa) back-pressure. The cooked starch was then put into a reaction kettle and cooled to 55° C. The pH of the solution was adjusted to 4.0 by adding 3:1 water:HCl. 0.2% isoamylase based on starch weight was added to start the debranching reaction. After 24 hour's reaction at pH 4.0 and 55° C., the pH was adjusted to 6.0 using 3% NaOH, and the sample was heated to 85° C. for 20 minutes to denature the enzyme. Then, the heat was shut off, and the sample was cooled to room temperature and crystallized overnight (16 hours). A sample cake was obtained following filtration and the product was air-dried.

B. 4 kg of Amioca™ 50 starch (acid converted waxy maize starch commercially available from National Starch and Chemical Company, Bridgewater, N.J., U.S.A) was slurried in 6 liters of water. The slurry pH was adjusted to 4.0 by adding 3:1 water:HCl. The sample was then jet-cooked and placed in a reaction container and the temperature was cooled to 55° C. 0.2% isoamylase was added and the reaction was allowed to proceed for 24 hours. The pH was adjusted to 2.0 by adding 3:1 water:HCl and held for 30 minutes to kill the enzyme. The pH was neutralized to 6.0 using 3% NaOH. The sample was cooled to room temperature and crystallized overnight (16 hours). A sample cake was obtained by filtration and the sample was air-dried.

C. The method of Example 1B was repeated with the exception that the starch was FloMax™ 5 starch (acid converted waxy maize starch commercially available from National Starch and Chemical Company).

D. 1.8 kg of waxy maize starch was slurried in 5.4 liters of water. The slurry was jet-cooked with full steam at 310–315° F. (154.4–157.2° C.) and 80 psi ($5.52 \times 10^5$ Pa) back-pressure. Under constant agitation, the cooked starch solution was diluted to 10% solids and put into a reaction container in a 55° C. waterbath. The sample pH was adjusted to 4.0 by adding 3:1 water:HCl. 0.2% isoamylase based on the dry starch weight was added to start the debranching reaction, maintaining the sample temperature at 55° C. After the sample DE reached 7.5 (about 8 hours reaction), pH was dropped to 2.0 for 30 minutes to denature the enzyme, and then increased to 6.0 using 3% sodium hydroxide. The sample was then cooled to room temperature and crystallized overnight (16 hours). A sample cake was obtained by filtration and the sample was air-dried.

DSC and resistant starch content were obtained for these samples. Table 1 summarizes the results.

TABLE 1

| Sample | RS % | DSC | | | |
|---|---|---|---|---|---|
| | | To (° C.) | Tp (° C.) | Tc (° C.) | ΔH (J/g) |
| 1A | 84.9 | 120.5 | 127.7 | 134.3 | 26.6 |
| 1B | 75.2 | 76.6 | 110.9 | 131.8 | 39.7 |
| 1C | 76.6 | 87.7 | 111.9 | 131.8 | 35.5 |
| 1D | 81.9 | 70.8 | 97.7 | 112.1 | 35.0 |

All samples showed more than 70% RS. All samples have higher than 110° C. peak temperature by DSC.

Example 2

Preparation of Resistant Potato Starch

Three kilograms of low amylose potato starch (commercially available from Lyckeby in Germany) was slurried in 9 liters of water and the sample was jet-cooked with full steam. The cooked starch solution was cooled to 55° C. and the pH was adjusted to 4.0 using 3:1 water:HCl. 0.2% isoamylase based on starch weight was added to start the debranching reaction. After 24 hours reaction time, the sample pH was increased to 5.5 with 3% NaOH, and heated to 85° C. in a boiling water bath for 20 minutes to denature the enzyme. The sample was cooled to room temperature overnight (16 hours) to crystallize the product. A sample cake was obtained by filtration and the sample was air-dried. Table 2 summarizes the resistant starch content and DSC results.

TABLE 2

| Sample | RS % | DP | DSC | | | |
|---|---|---|---|---|---|---|
| | | | $T_o$ (° C.) | $T_p$ (° C.) | $T_c$ (° C.) | $\Delta H$ (J/g) |
| 2 | 85.6 | 17 | 96.6 | 112.4 | 126.7 | 32.7 |

The debranched and crystallized low amylose potato sample showed more than 70% RS and had a peak temperature of greater than 110° C. by DSC.

Example 3

Process Tolerance of Resistant Starch

Several of the debranched resistant starches were processed using the low moisture model and the resistant starch of each is shown compared to that of the unprocessed starch. The results are shown in Table 3, below.

TABLE 3

| Sample | % RS pre-processing | % RS post-processing |
|---|---|---|
| 3A | 75.2 | 81.5 |
| 3B | 74.2 | 81.0 |
| 3C | 76.6 | 79.7 |

As can be seen from Table 3, the starches of the present invention are process tolerant in that the resistant starch content is not destroyed.

We claim:

1. A resistant starch composition prepared by completely debranching a low amylose starch comprising highly crystalline, fully debranched linear α-glucans, wherein the composition is characterized by
   a) a resistant starch content of at least about 70% by weight;
   b) a dextrose equivalent greater than about 4.0;
   c) a peak melting point temperature, $T_p$ as measured by DSC, of at least about 90° C.; and
   d) an enthalpy, $\Delta H$ as measured by DSC of at least 30 J/g.

2. The composition of claim 1, wherein the low amylose starch comprises no more than about 5% amylose by weight.

3. The composition of claim 1, wherein the dextrose equivalent of the composition is greater than about 5.0.

4. The composition of claim 1, wherein the dextrose equivalent of the composition is greater than about 6.0.

5. The composition of claim 1, wherein the resistant starch content of the composition is at least about 75% by weight.

6. The composition of claim 1, wherein the peak melting point temperature of the composition is at least about 100° C.

7. The composition of claim 1, wherein the peak melting point temperature of the composition is at least about 110° C.

8. The composition of claim 1, wherein the low amylose starch is selected from the group consisting of maize, potato, cassava, and rice.

9. A method of making the composition of claim 1 comprising:
   a) fully debranching a low amylose starch using isoamylase;
   b) allowing the debranched starch to crystallize; and
   c) drying the highly crystalline debranched starch.

10. The method of claim 9, wherein the low amylose starch comprises at least 95% amylopectin by weight.

11. The method of claim 9, wherein the dextrose equivalent of the composition is greater than about 5.0.

12. The method of claim 9, wherein the dextrose equivalent of the composition is greater than about 6.0.

13. The method of claim 9, wherein the composition contains at least about 75% resistant starch by weight.

14. The method of claim 9, wherein the peak melting point temperature of the composition is at least about 100° C.

15. The method of claim 9, wherein the peak melting point temperature of the composition is at least about 110° C.

16. The method of claim 9, wherein the low amylose starch is a maize, potato, cassava, and rice.

17. An edible product comprising the composition of claim 1.

18. The edible product of claim 17, wherein the product is a prebiotic supplement.

* * * * *